United States Patent [19]

Semrad

[11] Patent Number: 4,813,929

[45] Date of Patent: Mar. 21, 1989

[54] CHEST TUBE DEVICE AND METHOD OF INSERTING DEVICE

[76] Inventor: Neal Semrad, 2180 Cedarhurst Dr., Los Angeles, Calif. 90027

[21] Appl. No.: 16,261

[22] Filed: Feb. 19, 1987

[51] Int. Cl.$^4$ ............................................. A61M 31/00
[52] U.S. Cl. ...................................... 604/51; 604/158; 604/161; 604/164; 604/170; 128/768
[58] Field of Search ...................................... 604/49–54, 604/264, 280, 158–173, 317; 128/748, 768, 772

[56] References Cited

U.S. PATENT DOCUMENTS

| | | | |
|---|---|---|---|
| Re. 31,855 | 3/1985 | Osborne | 604/161 |
| 3,960,153 | 6/1976 | Carey et al. | 604/164 |
| 4,230,123 | 10/1980 | Hawkins, Jr. | 604/51 |
| 4,291,694 | 9/1981 | Chai | 604/161 |
| 4,351,333 | 9/1982 | Lazarus et al. | 604/51 |
| 4,636,199 | 1/1987 | Victor | 604/164 |
| 4,650,472 | 3/1987 | Bates | 604/158 |
| 4,687,469 | 8/1987 | Osypka | 604/161 |

Primary Examiner—C. Fred Rosenbaum
Assistant Examiner—Mario Costantino
Attorney, Agent, or Firm—John E. Wagner

[57] ABSTRACT

A method and assembly of components for effecting closed chest thoracostomy includes insertion of a large bore needle into the chest cavity following local anesthesia. A guide wire is inserted into the pleural cavity through the needle and the needle is removed. An incision of one to one and one-half centimeters is then made parallel to the ribs and a pleural access catheter is delivered over the guide wire into the cavity. The guide wire is removed and a chest tube is introduced through the pleural access catheter, which is then split off and removed from around the chest tube. The chest tube is then sewn in place, dressed and placed to drainage. A thoracostomy kit includes the necessary instruments to effect the procedure in a sealed sterile package.

16 Claims, 3 Drawing Sheets

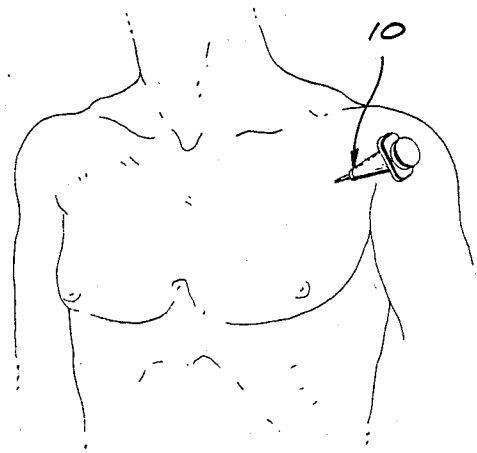
FIG. 2
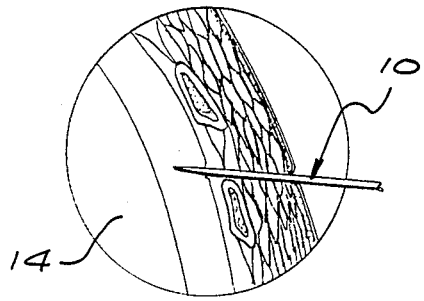
FIG. 2A
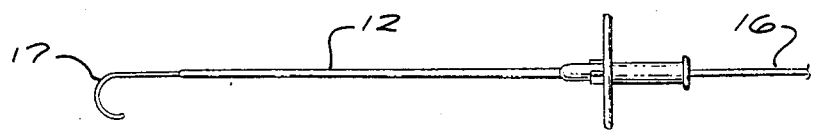
FIG. 3
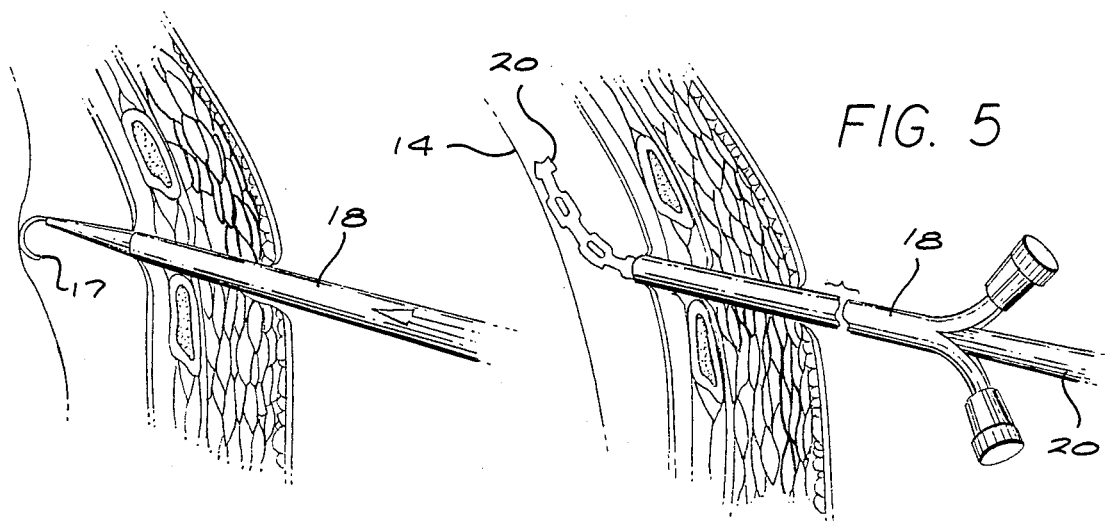
FIG. 4
FIG. 5
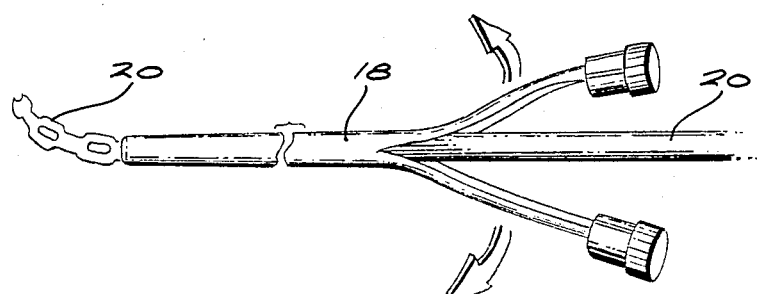
FIG. 6

CHEST TUBE DEVICE AND METHOD OF INSERTING DEVICE

BACKGROUND OF THE INVENTION

The insertion of chest tubes into the pleural cavity of patients suffering from a number of different conditions is a well-established procedure. The indications for closed thoracostomy chest tube insertion vary from the treatment of malignant pleural effusions to the life-saving evacuation of a traumatic hemopneumothorax and the use of closed thoroacostomy chest tube insertion has been well known for decades.

Although the process is considered to be basically effective and safe, there remain certain distinct disadvantages. A fairly large incision with vigorous blunt dissection with clamp or probe is used, sometimes with less than precisely controlled force to enter the pleural cavity. Alternatively, a smaller incision and a trocar within a chest tube that is effectively speared into the patient is sometimes used. With the latter procedure it is possible to pierce the lung and it is often difficult to assure placement in the pleural space desired. Further, the force (and its awkward application some distance from the site of penetration into the thorax) necessary to pierce the chest is sometimes difficult to control. With either of the above techniques, it has been difficult to aim the chest tube with any accuracy (anterior, posterior, inferior, superior or some combination), and this is important for its therapeutic advantage.

Not the least of the problems associated with this prior art technique, are that the patients find the procedure uncomfortable and frequently unnerving when they observe their doctor exerting himself or herself to generate the force required for insertion by the above techniques. Bleeding from the wound and/or from inadvertent puncture of vessels can be a problem. In the trauma patient, the time required to gather equipment and perform the procedures can be critical.

In situations where it is necessary to inject material into the bloodstream, it has been known to place or replace catheters over guide wires. Applicant is not aware of procedures wherein catheters have been placed over guidewires in connection with closed thoracostomy chest tube insertions.

BRIEF SUMMARY OF THE INVENTION

In a patient with air, blood and/or fluid in the pleural cavity a large bore needle with syringe is inserted into this space following local anesthesia. Through this large bore needle, a guide wire is then placed into the pleural space and the needle removed. An incision is then made parallel to the ribs over the guide wire approximately one to one and one-half cm. in length, depending on the size of pleural cavity access catheter and chest tube to be introduced. The access catheter is then delivered into the cavity over the guide wire with firm, controlled pressure. Following removal of the guide wire and obturator of the pleural cavity access catheter, the chest tube is then rapidly introduced via the access catheter which is then split off from around the chest tube. The chest tube is sewn in place, dressed, and placed to drainage as usual.

BRIEF DESCRIPTION OF THE DRAWING

FIG. 2 is a partial front view of the chest area of a patient showing the manner in which the large bore needle may be inserted;

FIG. 2-A is a cross-section of a portion of the chest wall showing the manner in which the needle is inserted between the ribs into the pleural cavity;

FIG. 3 is an illustration of the large bore needle with the guide wire inserted therethrough;

FIG. 4 is a partial cross-section of a chest cavity wall showing the manner in which the catheter is delivered into the cavity over the guide wire;

FIG. 5 is a view similar to FIG. 3 showing the insertion of the chest tube through the catheter into the pleural cavity;

FIG. 6 is an illustration showing the manner in which the catheter is split off from the chest tube after the chest tube is inserted.

DETAILED DESCRIPTION OF THE PREFERRED EMBODIMENT

Figure 1:
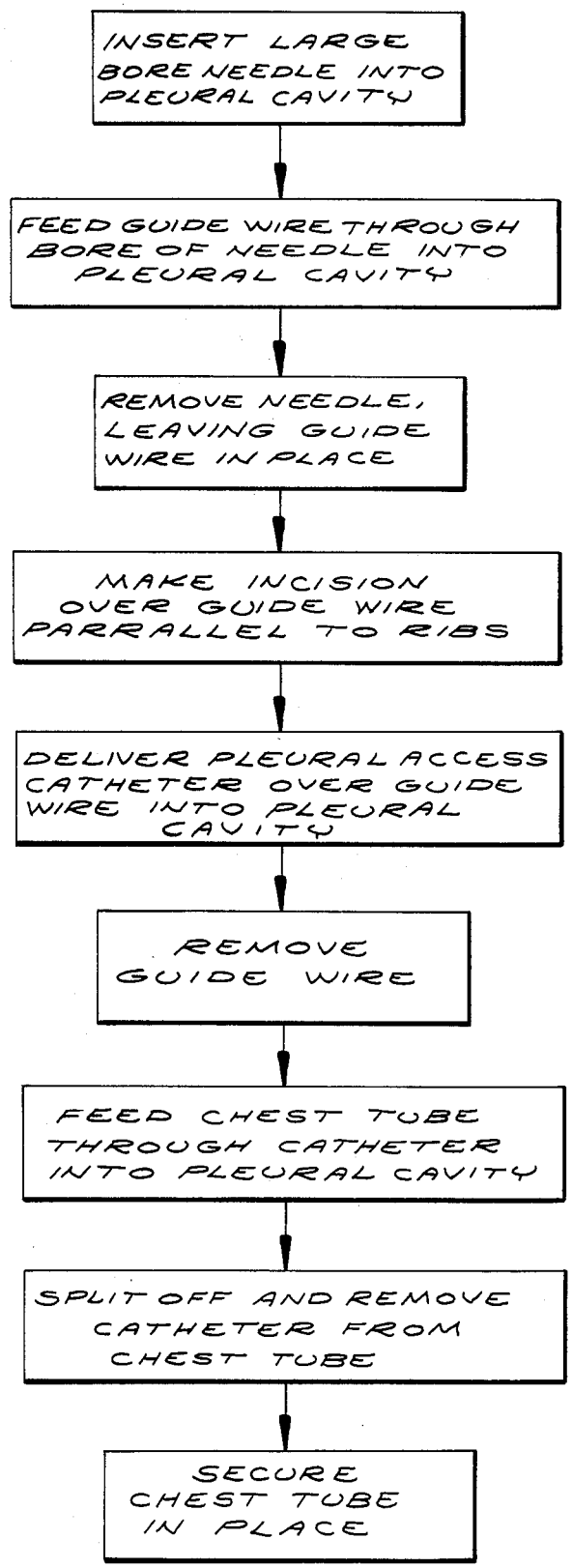
FIG. 1 is a flow diagram showing the order of the steps in my invention.

FIG. 1 is a flow diagram showing the order of the essential steps in the closed thorescotomy chest tube insertion procedure according to my invention. As can be seen from the diagram, the steps, in order, involve inserting a large bore needle in a desired location in the chest cavity, feeding a guide wire through the needle into the chest cavity, removing the large needle leaving the guide wire in place, making an incision parallel to the ribs over the guide wire, delivering a pleural access catheter over the guide wire into the pleural cavity, removing the guide wire, feeding the chest tube into the pleural cavity through the catheter, splitting off and removing the catheter from the chest tube, and securing the chest tube in place.

Referring now to FIGS. 2 and 2A, it will be seen that the large bore needle 10 may be inserted into the chest cavity where desired at a suitable location between the ribs. Needle 10 is preferably tapered or wedge shaped to aid in penetration. FIG. 1A illustrates the position which the large bore needle 10 might assume between the ribs within the pleural cavity and yet short of the position where it might puncture the lungs shown at 14. The location of insertion of the needle is of course, determined by taking into consideration the anatomy and pathophysiology of the particular patient. For example, with a malignant pleural effusion, the needle might be placed in the mid-axilliary line, slightly anterior, above the ninth rib, and directly above the diaphragm and posteriorily.

After insertion of the needle, the guide wire 16 is fed through the needle, as shown in FIG. 3. It should be stressed that the needle and guide wire should be aimed in the direction in which the chest tube is to lie, irrespective of the location on the chest wall that is penetrated. It should be noted that guide wire 16 is comparatively flexible and is in the form of a very small helically wound spring, having the outboard bend 17 preformed to avoid puncturing any tissue.

Following insertion of the guide wire 16, an incision is made parallel to the ribs over the guide wire approximately 1 to 1½ cm. in length, depending on the size of the pleural cavity access catheter and the chest tube to be introduced. As shown in FIG. 3, the access catheter 18 is then delivered into the cavity over the guide wire with firm controlled pressure. Following removal of the guide wire 12 and obturator of the pleural cavity access catheter, the chest tube 20 is then rapidly introduced through the access catheter 18. Catheter 18 is then split off from around the chest tube 20, as shown in FIG. 5. The chest tube is then sewn in place, as described above. Since the size of the wound created by this procedure is quite small, at the time of removal of the chest tube a STERI-STRIP* skin closure is all that is required for these smaller wounds.

*Trademark of 3M Corporation

Figure 7:
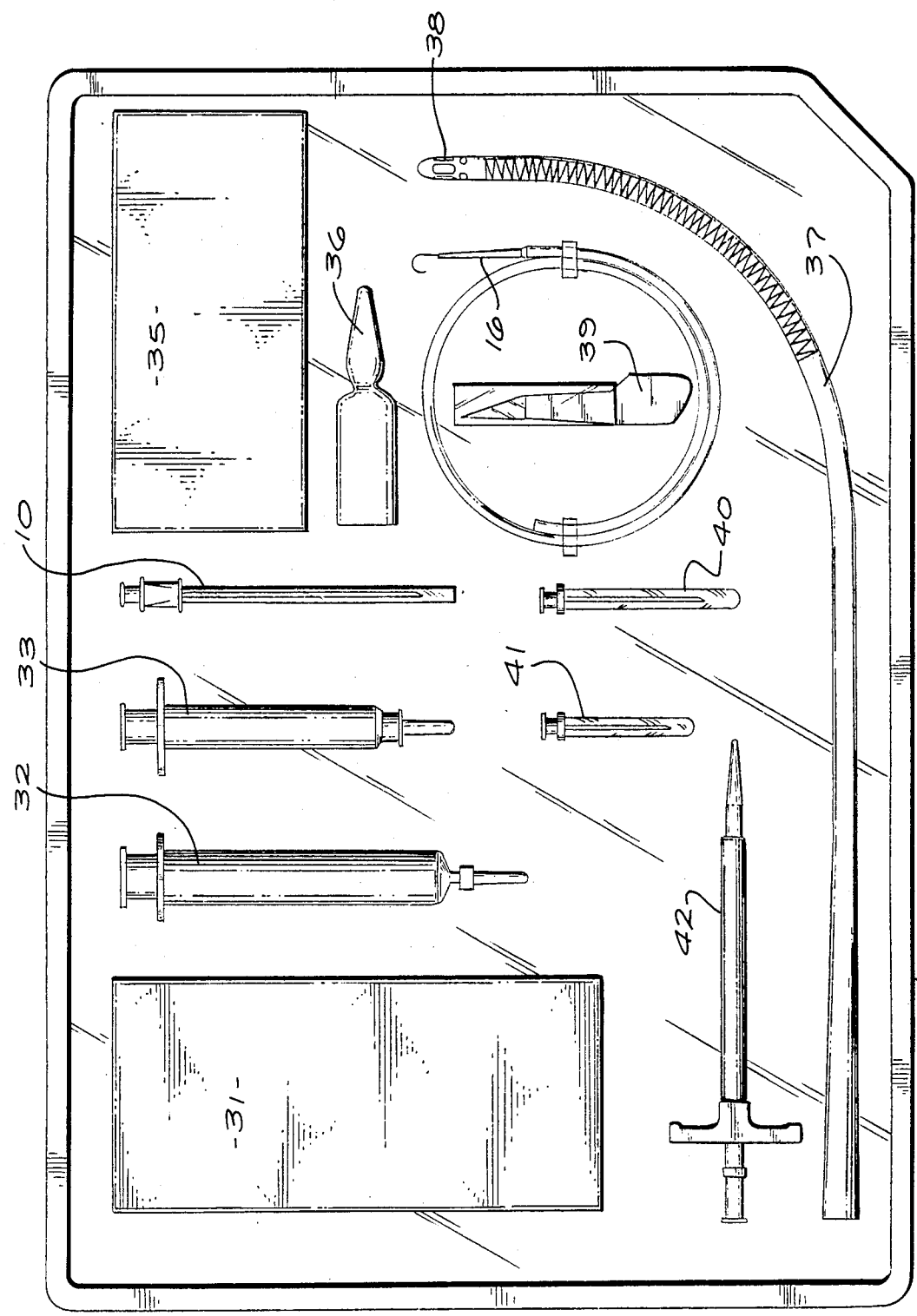
FIG. 7 is a plan view of a packaged thoracostomy kit suitable for performing the procedure described with reference to FIGS. 1-6.

FIG. 7 is a plan view of a packaged kit including instruments used in performing the above procedure. Somewhat similar kits have been available for use in procedures when catheters are introduced into veins or arteries and take the form of a molded plastic tray having formed pockets or indentations for receiving the specific items needed in the procedure. A cover is sealed to the tray after the instruments and other items are located in their proper pockets. The entire assembly is sterilized and remains sterile until opened for use.

Applicant has devised a packaged kit specifically designed for the thoracostomy procedure described above. In this kit a molded plastic tray 30 is formed with suitable pockets or recesses for receiving a number of components. A large rectangular recess contains a package 31 containing conventional P/I swab sticks, 3 pack. A 10 cc. syringe 32 and a 5 cc. syringe 33 are also placed in mating pockets. Item 10 is a thinwall needle, 18 gauge×2¾ in. placed in a protective tube. A suitable suture and needle for use in securing the chest tube as described above are packaged in a rectangular package 35 adjacent a small container 36 containing lidocaine 1%, 5 cc. Adjacent the container 36 is a coiled and sheathed guide wire 16 which encircles a scalpel 39. A pair of smaller syringe needles 25 gauge and 20 gauge in suitable containers are shown in numerals 40 and 41 respectively. A chest tube 37 is shown having openings 38 at its right end for drainage. Item 42 is the pleural cavity access catheter which is placed over the guidewire as described above to provide access for the chest tube 37. The smaller syringe 33 is used with needle 41 to administer the lidocaine locally. The larger syringe 32 is or may be used with needle 40 to make an initial penetration to assess the location in the pleural cavity for the larger needle 10 and guidewire 16.

A considerable number of advantages result from application of the above technique. As contrasted with the prior art technique, insertion is very rapid, vascular structures are easily avoided and the aiming of the direction of the chest tube is facilitated. Further, chest tubes can be placed anywhere through the chest wall so that patients do not have to lie on them and so that drainage can be increased. Another advantage is that a softer chest tube can be used, since it does not have to have sufficient rigidity to survive the force of clamping or chest wall penetration which also reduces the incidence of pulmonary lacerations and fistulae. A still further advantage is that the brute strength of the operator becomes less important and patient anxiety and discomfort from the summoning of such strength and action is thereby minimized. By tunnelling the needle and guide wire over the rib prior to penetrating the chest wall above the rib, a flap is created that helps seal the thoracostomy site on removal, the defect is much smaller to begin with as it is only the diameter of the access catheter. Also minimal instruments are necessary making the new procedure cost-effective.

With the above description in mind, reference is made to the claims appended hereto for a definition of the scope of the invention.

What is claimed is:

1. A method of accomplishing closed thoracostomy chest tube insertion comprising the steps of:
   (1) Inserting a large bore needle into a desired location in the pleural cavity,
   (2) Feeding a guidewire through the bore of the needle into the pleural space,
   (3) Removing the needle, leaving the guidewire in place,
   (4) Making an incision parallel to the ribs over the guidewire,
   (5) Delivering a pleural access catheter over the guide wire into the pleural cavity,
   (6) Removing said guidewire,
   (7) Feeding a chest tube through said pleural access catheter into the pleural cavity wherein said chest tube follows the path of the pleural access catheter,
   (8) Splitting off and removing the catheter from the chest tube, and
   (9) Securing the chest tube in place.

2. A method of accomplishing closed thoracostomy chest tube insertion as claimed in claim 1 wherein said large bore needle is formed with a wedge-shaped point to aid in penetration.

3. A method of accomplishing closed thoracostomy chest tube insertion as claimed in claim 1 wherein said chest tube is removed and the remaining wound is secured by means of an adhesive skin closure.

4. A method of accomplishing closed thoracostomy chest tube insertion as claimed in claim 1 including the further steps of removing said chest tube when desired and dressing the remaining wound with an adhesive skin closure.

5. A chest tube insertion kit in a sealed package to assure sterile condition including at least:
   a large bore needle with syringe,
   a guide wire of diameter suitable to pass through said bore,
   a scalpel
   an access catheter including means for splitting said catheter, and
   a chest tube of suitable diameter to pass through said catheter.

6. A chest tube insertion kit as claimed in claim 5 wherein said kit further includes a supply of a local anesthetic, and a syringe for administering said anesthetic.

7. A chest tube insertion kit as claimed in claim 5 wherein said kit further includes a needle and a suture and wherein said sealed package is comprised of a molded tray having a cover.

8. For use in performing closed thorascostomy chest tube insertion an assembly of interrelated instruments comprising a hollow needle, a flexible guide wire of diameter to pass through said needle, said guide wire being formed as a coil of many turns of very fine wire and having a curved end to avoid puncturing tissue, a scalpel for making an incision over said guide wire, a pleural access catheter which is configured to be split longitudinally for insertion over said guide wire into the pleural cavity and a chest tube which is softer than said pleural access catheter and of a diameter which will pass through said pleural access catheter.

9. An assembly as claimed in claim 8 further including a molded tray having a cover, said instruments are carried in said tray, and said instruments, said tray and said cover are sterilized.

10. An assembly as claimed in claim 9 further including a supply of local anesthetic material and a needle and syringe for administering said material.

11. An assembly as claimed in claim 8 further including a syringe to be attached to said hollow needle.

12. An assembly as claimed in claim 11 further including a needle and suture for securing said chest tube in place.

13. An assembly as claimed in claim 8 further including a syringe for attachment to said hollow needle, a supply of local anesthetic material and a needle and syringe for administering said local anesthetic, and a needle and suture for securing said chest tube in place.

14. A kit for use in performing closed thoracostomy chest tube insertion including a tray and a plurality of components including a guidewire, a needle of suitable size to contain said guidewire and a syringe for use in guiding said needle, a scalpel, a small container of suitable anesthetic and a needle and syringe for administering said anesthetic, a pleural cavity access catheter of material which tears readily in a longitudinal direction and a chest tube of diameter which will pass through said pleural cavity access catheter, wherein said tray is formed with indentations to hold and secure said components and said cover is sealed to said tray, all of said components, said tray and said cover being sterilized.

15. A kit as claimed in claim 14 wherein said tray further includes an additional syringe and needle for making a preliminary determination of location for the chest tube.

16. A kit as claimed in claim 14 wherein said tray further includes a suture and needle for securing the chest tube in place.

* * * * *